US005280785A

United States Patent [19]

Fujima

[11] Patent Number: 5,280,785

[45] Date of Patent: Jan. 25, 1994

[54] DIVING SNORKEL

[75] Inventor: Taro Fujima, Tokorozawa, Japan

[73] Assignee: Tabata Co., Ltd., Tokyo, Japan

[21] Appl. No.: 48,180

[22] Filed: Apr. 20, 1993

Related U.S. Application Data

[63] Continuation-in-part of Ser. No. 941,781, Sep. 8, 1992, abandoned.

[51] Int. Cl.[5] ..................... B63C 11/16; A61M 16/00; A62B 9/02; A62B 9/06

[52] U.S. Cl. ........................... 128/201.11; 128/207.16

[58] Field of Search ...................... 128/200.24, 201.27, 128/201.11, 200.29, 207.14, 911, 201.26, 207.16, 207.17

[56] References Cited

U.S. PATENT DOCUMENTS

| | | | |
|---|---|---|---|
| 3,993,060 | 11/1976 | Mitchell | 128/201.11 |
| 4,278,080 | 7/1981 | Schuch | 128/201.11 |
| 4,655,212 | 4/1987 | Delphia | 128/201.11 |
| 4,805,610 | 2/1989 | Hunt | 128/201.11 |
| 4,872,453 | 10/1989 | Christianson | 128/201.11 |
| 4,879,995 | 11/1989 | Christianson | 128/201.11 |
| 4,910,806 | 3/1990 | Baker | 128/201.11 |
| 5,117,817 | 6/1992 | Lin | 128/201.11 |
| 5,143,059 | 9/1992 | Delphia | 128/201.11 |

*Primary Examiner*—David A. Wiecking
*Assistant Examiner*—Kimberly L. Asher
*Attorney, Agent, or Firm*—Fred Philpitt

[57] ABSTRACT

A diving snorkel having a ventilating portion comprising an assembly of a first pipe portion and a second pipe portion extending in parallel to and communicating with each other, and a main pipe of which the upper end is connected to the first pipe portion, wherein the second pipe portion is provided at its upper end with an air inlet and at its lower end provided with means to prevent the undesirable flow of water into the main pipe 2 through the air inlet as a diver is in the water.

7 Claims, 7 Drawing Sheets

DIVING SNORKEL

RELATED APPLICATION

This is a continuation-in-part of copending application Ser. No. 07/941,781 filed Sep. 8, 1992 now abandoned and the benefits of 35 USC 120 are claimed relative to it.

BACKGROUND OF THE INVENTION

This invention relates to diving snorkels (referred to hereinafter simply as "snorkel" or "snorkels") allowing a diver to breathe as the diver swims under water.

Typical known snorkels generally comprise a ventilating portion including an air inlet, a mouthpiece, a draining portion having a non-return valve, and a main pipe connecting these air inlet, mouthpiece and draining portions, said ventilating portion being positioned above the water surface while the mouthpiece and the draining portion are positioned below the water surface during use of the snorkel. Once a diver has surfaced and the air inlet of the snorkel has been exposed above the water surface, water which has entered the snorkel is partially expelled out from the non-return valve under the effect of a differential water pressure until the water level within the snorkel comes down to the water surface. The non-return valve is adapted to be normally opened downward with respect to the water surface. The diver may intensely breathe out through the mouthpiece to expel out the rest of the water still remaining within the snorkel from the draining portion and the air inlet. Arrangements of such known snorkels are disclosed, for example, in Japanese Utility Model Application disclosure Gazette No. 1974-33039 and U.S. Pat. No. 4,278,080.

When the snorkel is washed by a wave during its use, free breathing by a diver is sometimes hindered by a quantity of water flowing into the snorkel through the air inlet. While any quantity of water flowing into a conventional snorkel can be expelled outwardly therefrom by intense exhalation by the diver, it has been difficult for the conventional snorkel to prevent water from flowing into the snorkel. To solve this problem, various improvements have been proposed. For example, U.S. Pat. No. 4,879,995 discloses an arrangement comprising a first pipe having an air inlet and a second pipe having a mouthpiece wherein the first pipe has a flared end provided with a non-return valve and the second pipe is connected substantially in series with said flared end of the first pipe. This arrangement allows a quantity of water that has flowed into the snorkel to be drained out through the non-return valve with no portion of said quantity reaching the mouthpiece. However, said flared end has a construction which is complicated, resulting in that both the assembly and maintenance of such a snorkel is a time-consuming job.

Accordingly, it is a principal object of the present invention to effectively inhibit the flow of water which otherwise might enter the main pipe by providing a relatively simple arrangement such that an assembly of first and second pipe portions extending in parallel to each other and communicating with each other is connected to the upper end of the snorkel's main pipe, wherein the wall of the second pipe portion serves as a dam adapted to inhibit the flow of water into the main pipe through a communication port provided between said first and second pipe portions.

The object set forth above can be achieved, according to one embodiment of the invention, by a diving snorkel comprising a ventilating portion provided with an air inlet adapted to be positioned above the water surface, a mouthpiece being positioned below the water surface a draining portion being provided with a first non-return valve adapted to be normally opened downward respect to the water surface, during use of the snorkel, and a main pipe connecting said air inlet with said mouthpiece and said draining portion, wherein said ventilating portion comprises a first pipe portion and a second pipe portion extending in parallel to each other and a communicating port provided to establish communication between these two pipe portions; wherein the first pipe portion has an upper end defined by a top wall and a lower end connected integrally with the main pipe; wherein the second pipe portion has an upper end defined by the air inlet and a lower end having an outlet that will permit the downward drainage of water through the second pipe portion; and wherein the port is provided between the air inlet and said outlet.

Preferably, the first pipe portion and the second pipe portion have a common inner wall separating these two pipe portions and the communicating port is at least partially defined in the first pipe portion by said common inner wall and the top wall.

With the snorkel constructed as described above, a side wall of the second pipe portion extends in front of the communicating port so as to at least partially conceal the port and functions as a dam or a barrier serving to obstruct the flow of water which otherwise might enter the main pipe through the communicating port. Even when the snorkel is washed by wave, the quantity of water flowing into the second pipe portion can be drained out through a non-return valve provided in the lower end of the second pipe portion.

BRIEF DESCRIPTION OF THE DRAWINGS

The invention will be described more in detail with reference to the attached drawings, in which.

DESCRIPTION OF THE PREFERRED EMBODIMENTS

Figure 1:
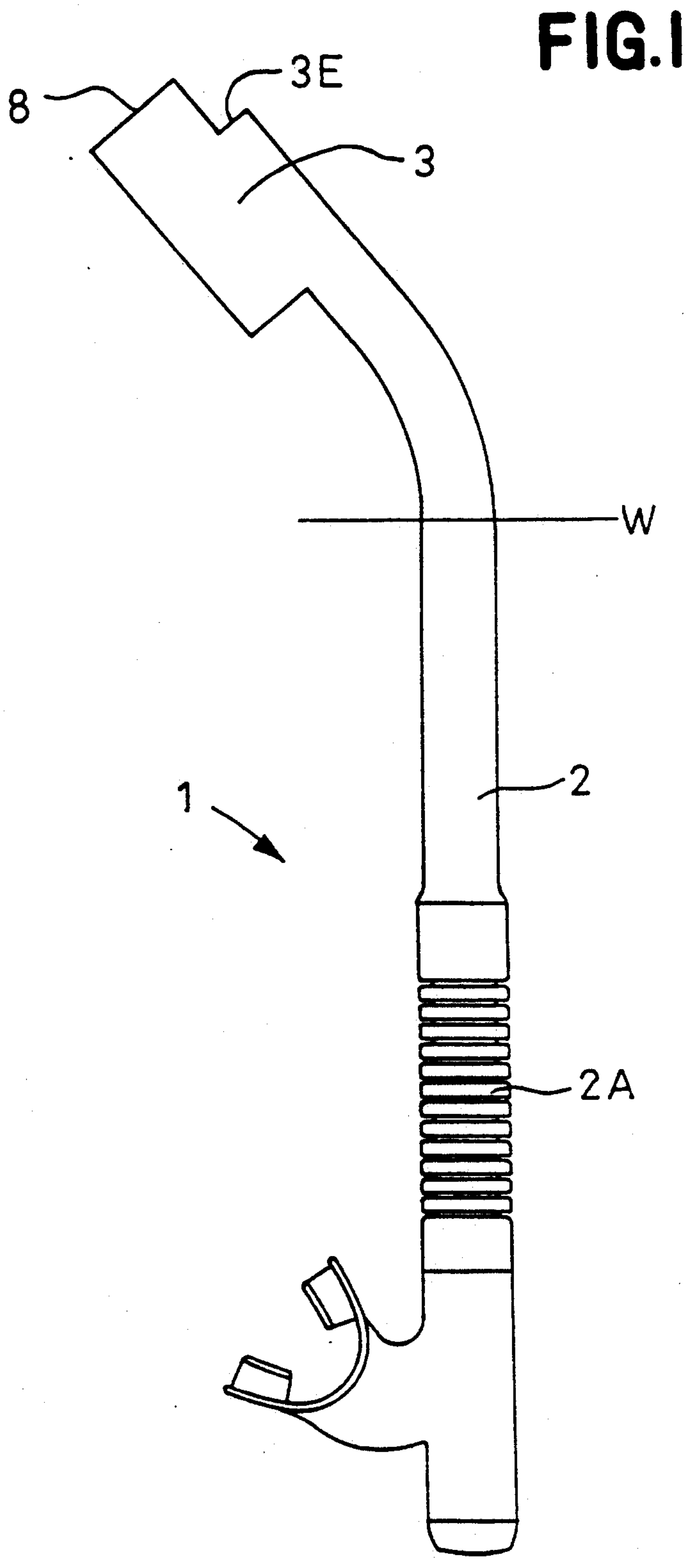
FIG. 1 is a side view of a snorkel constructed in accordance with the invention.
Figure 2:
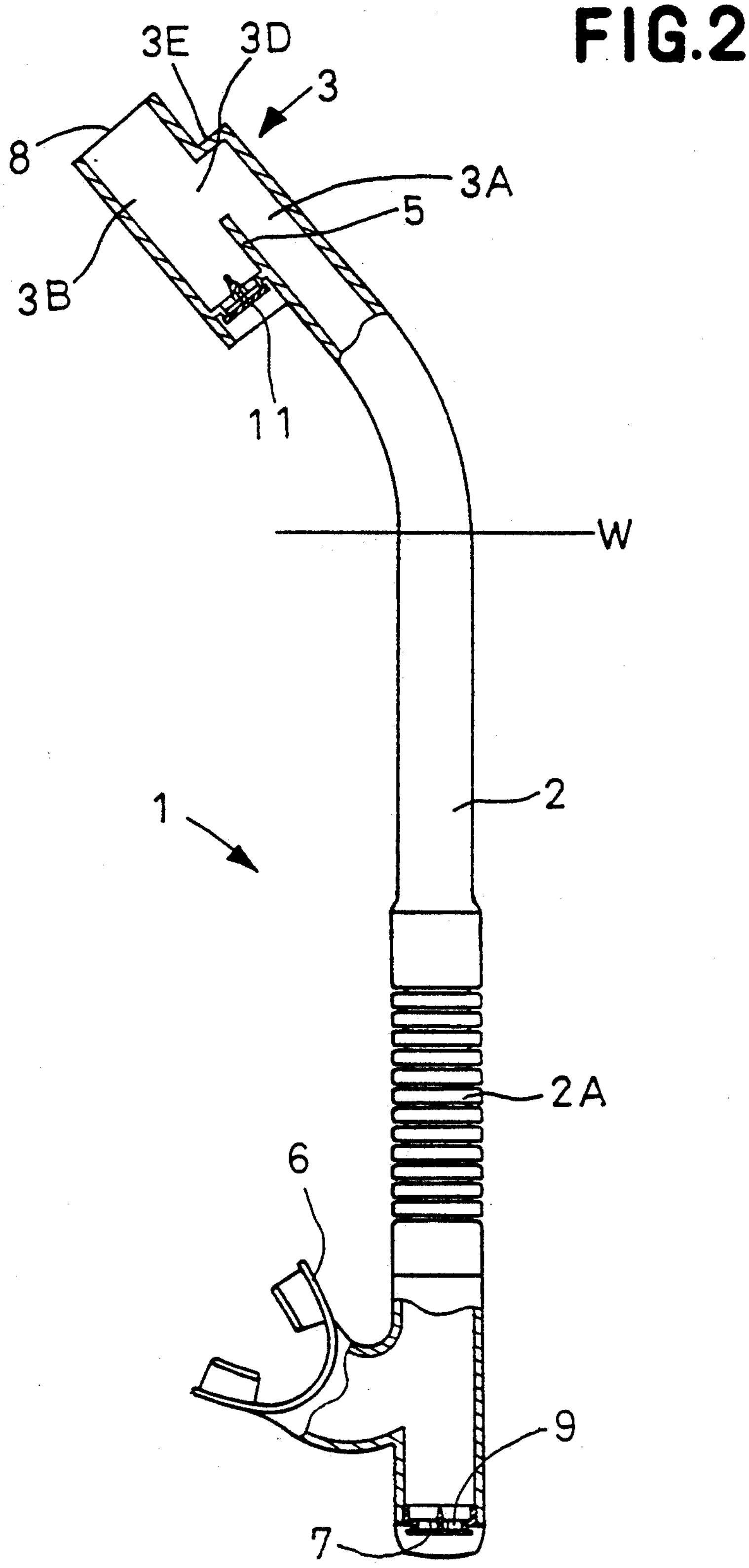
FIG. 2 is a side view showing, partially in sections, the snorkel of FIG. 1.

FIG. 1 is a side view of a snorkel 1 constructed according to the invention and FIG. 2 is a view similar to FIG. 1 but showing the internal structure of the snorkel partially in section. The letter W exemplarily designates the position of the water surface which is assumed during use of the snorkel 1. In its posture as shown, the snorkel 1 has a ventilating portion 3 comprising assembly of a first pipe portion 3A and a second pipe portion 3B arranged side-by-side with respect to each other and connected to an upper end of the main pipe 2. An inner pipe wall 5 common to the two pipe portions 3A, 3B separates them from each other and this inner pipe wall 5 is partially cut away so as to define a port 3D through which these two pipe portions 3A, 3B communicate with each other. A lower end of the main pipe 2 forks into two branches, one of which leads to a mouthpiece 6 and the other leads to a draining portion 9. The draining portion 9 is provided with a first non-return valve 7 adapted to be normally opened downward with respect to the water surface W, i.e., outward of the pipe 2. The pipe 2 includes a bellows-like structure 2A extending along an intermediate length thereof, making the pipe 2 flexible.

The first pipe portion 3A has an upper end provided with a top wall 3E extending transversely of an axis of the first pipe portion 3A and a lower end connected integrally with the main pipe 2.

The second pipe portion 3B has an upper end provided with an inlet 8 for the outside air and a lower end provided with a second non-return valve 11. This second non-return valve 11 is adapted to be normally opened outward of the second pipe portion 3B and thereby to drain water which has flowed into the upper end of the second pipe portion 3B.

The communicating port 3D is provided in the second pipe portion 3B between the air inlet 8 and the second non-return valve 11 so that the communicating port 3D is concealed behind the outer pipe wall of the second pipe portion 3B standing in front of the communicating port 3D. Thus, the outer pipe wall of the second pipe port 3B can obstruct a quantity of water which otherwise might wash into the first pipe portion 3A and the main pipe 2 through the communicating portion 3D. In the first pipe portion 3A the top wall 3E thereof and a portion 5 of the inner pipe wall define at least a part of the communicating port 3D.

The snorkel 1 of such construction is used with the air inlet 8 and the second non-return 11 being positioned above the water surface W and with the mouthpiece 6 and the draining portion 9 being positioned below the water surface W. When the top of the snorkel 1 is washed over by a wave, the second pipe portion 3B serves to at least partially obstruct the water flow which otherwise might enter the first portion 3A through the communicating port 3D. Also, when the snorkel 1 is washed by a wave from below, the water flow which otherwise might enter the first pipe portion 3A can be avoided because the second non-return valve 11 is always closed upward. In this manner a quantity of water having flowed through the air inlet 8 into the second pipe portion 3B is drained out through the second non-return valve 11 which minimizes the possibility that a quantity of water can accumulate within the second pipe portion 3B and overflow therefrom into the first pipe portion 3A through the communicating port 3D. Quantities of water which accumulate bit-by-bit in the lower end of the snorkel 1 can be expelled through the communicating port 3D into the second pipe portion 3B by intense exhalation by the diver into the mouthpiece 6 and the water then drained out of portion 3B through the non-return valve 11.

It can be understood from the foregoing description that the second pipe portion 3B functions like a sort of dam or screw to obstruct the water flow into the first pipe portion 3A through the communicating port 3D and thereby prevents the accumulation of much water in the main pipe 2 adjacent the mouthpiece 6 that would interrupt the smooth breathing by the diver.

Figure 3:
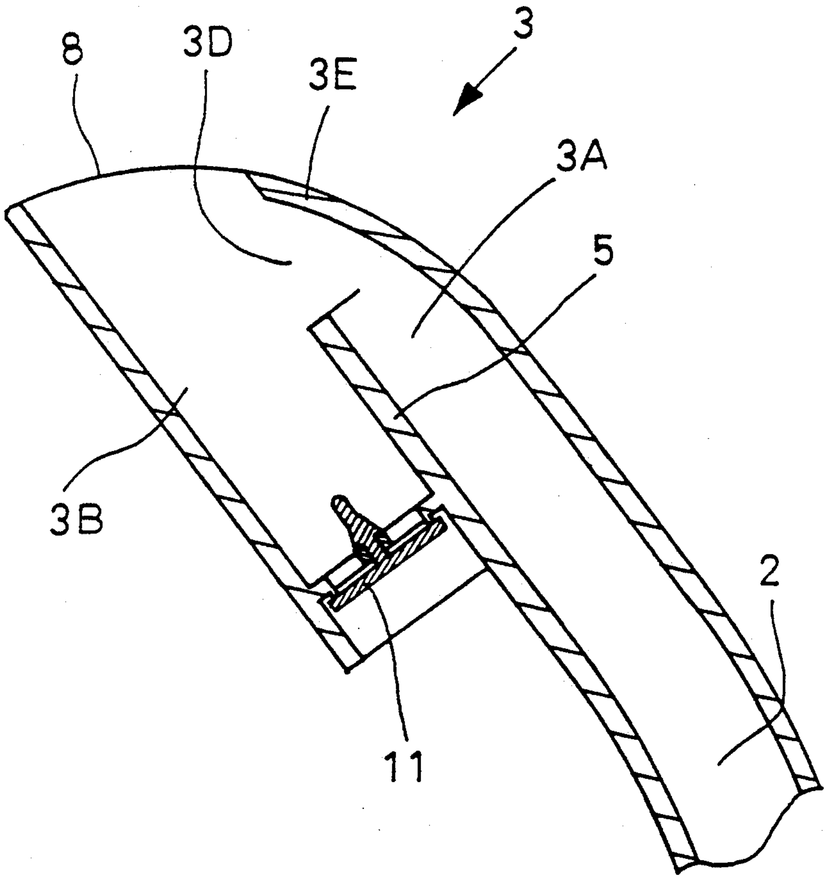
FIG. 3 is a fragmentary sectional view showing one of preferable embodiments of the snorkel.

FIG. 3 shows a fragmentary sectional view of another embodiment of the invention. In this embodiment, the top wall 3E is defined by a circular arc extending from the pipe wall obliquely with respect to the axis of the first pipe portion 3A and the air inlet 8 is provided as an extension of the top wall 3E. Accordingly, the air inlet 8 is defined at least partially by the top wall 3E and the pipe wall of the second pipe portion 3B. While the communicating port 3D tends to be somewhat closer to the air inlet 8 than in the case of FIG. 2, the pipe wall of the second pipe portion 3B effectively functions as a dam standing in front of the communicating port 3D by which the undesirable water flow is substantially obstructed.

The main pipe 2 as well as the first and second pipe portions 3A, 3B may be molded from suitable thermoplastic material and the first and second non-return valves 7, 11 as well as the bellows-like structure 2A and the mouthpiece 6 may be molded from urethane rubber or the like. While the first pipe portion 3A and the second pipe portion 3B may be molded in a form of single-piece component, these two portions may be molded as separate pieces, followed by bonding together, if their constructions are too complicated to be molded as a single-piece component.

According to the invention, the communicating port of the snorkel is arranged so as to be concealed behind the pipe wall of the second pipe portion which serves as a dam for the communicating port. This arrangement not only obstructs the water flow into the snorkel but also substantially eliminates the accumulation of water in the main pipe adjacent the mouthpiece. Prevention of the water flow can be further improved by arranging the first and second pie portions and the communicating port so as to establish such a deflected passage for ventilation as shown by the embodiments.

Figure 4:
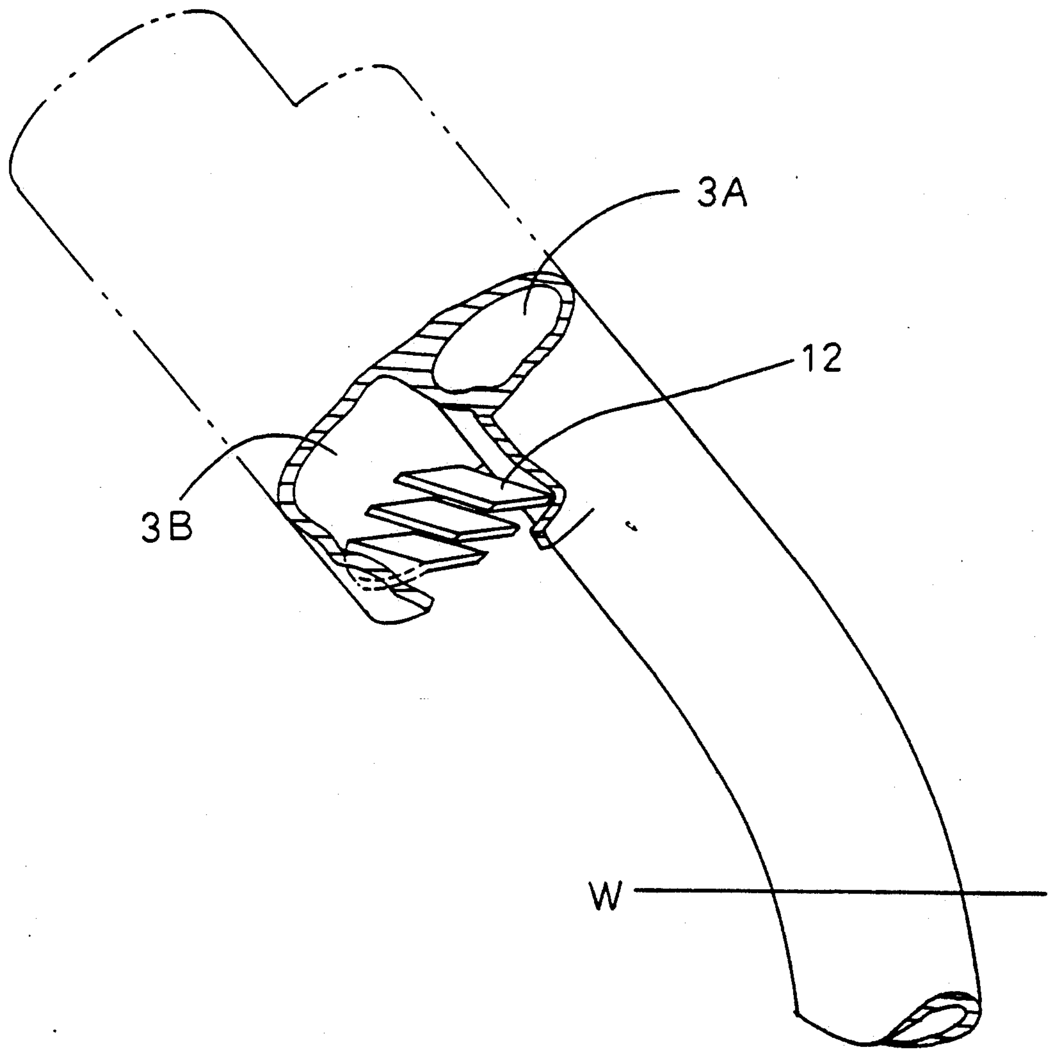
FIGS. 4 and 5 are partial cross sectional views illustrating another embodiment of the invention.
Figure 5:
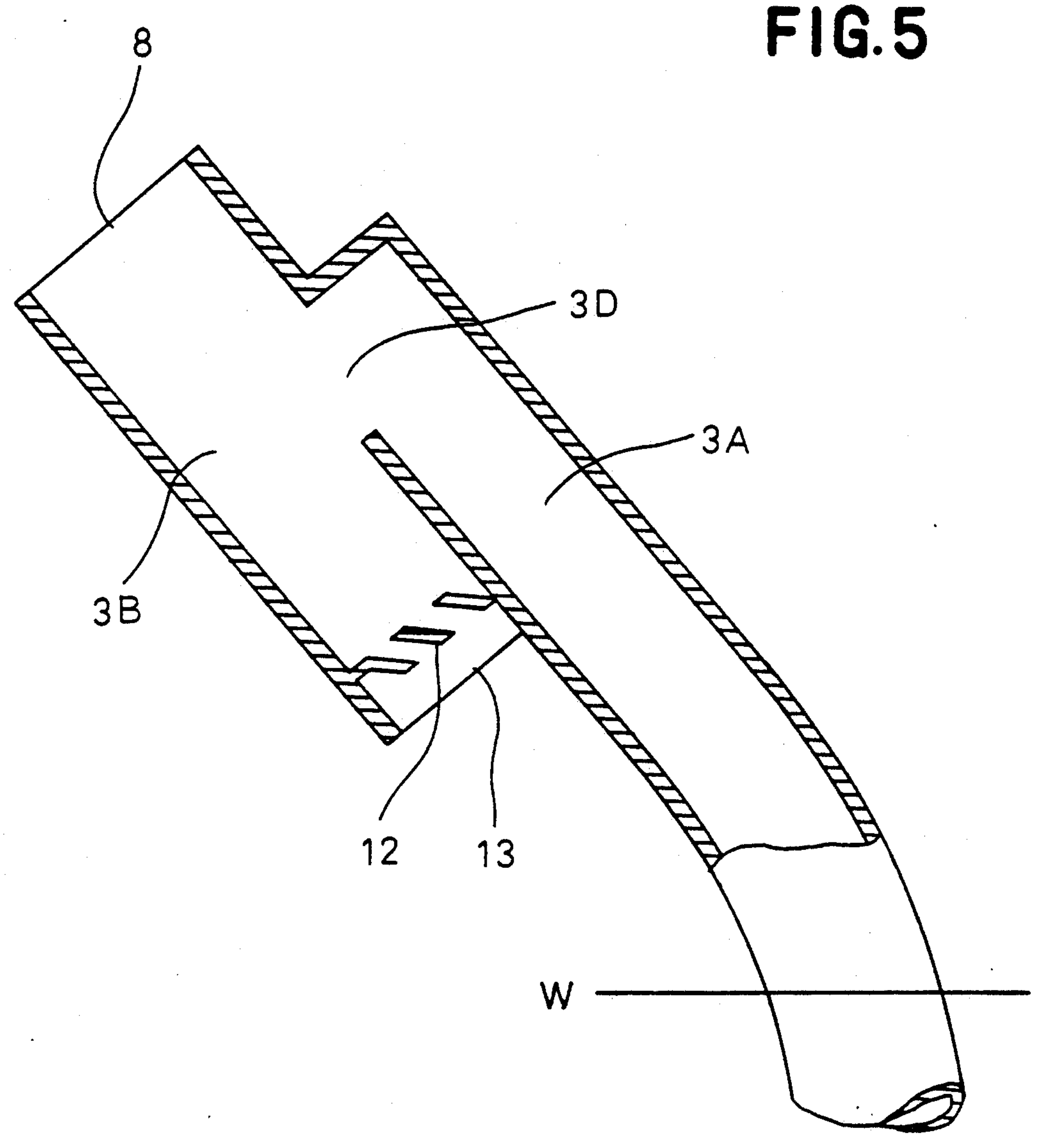

FIGS. 4 and 5 show another embodiment of the invention wherein the second non-return valve 11 of FIGS. 2 and 3 has been replaced with vanes 12 that extend across the lower end 13 of the second pipe portion 3B and which inhibit the upward flow of water through 13. As shown the vanes 12 are fixed in place, but the vanes can also be pivotally mounted so that in one position they can extend completely across the lower end 13 of said second pipe portion (3B).

Figure 6:
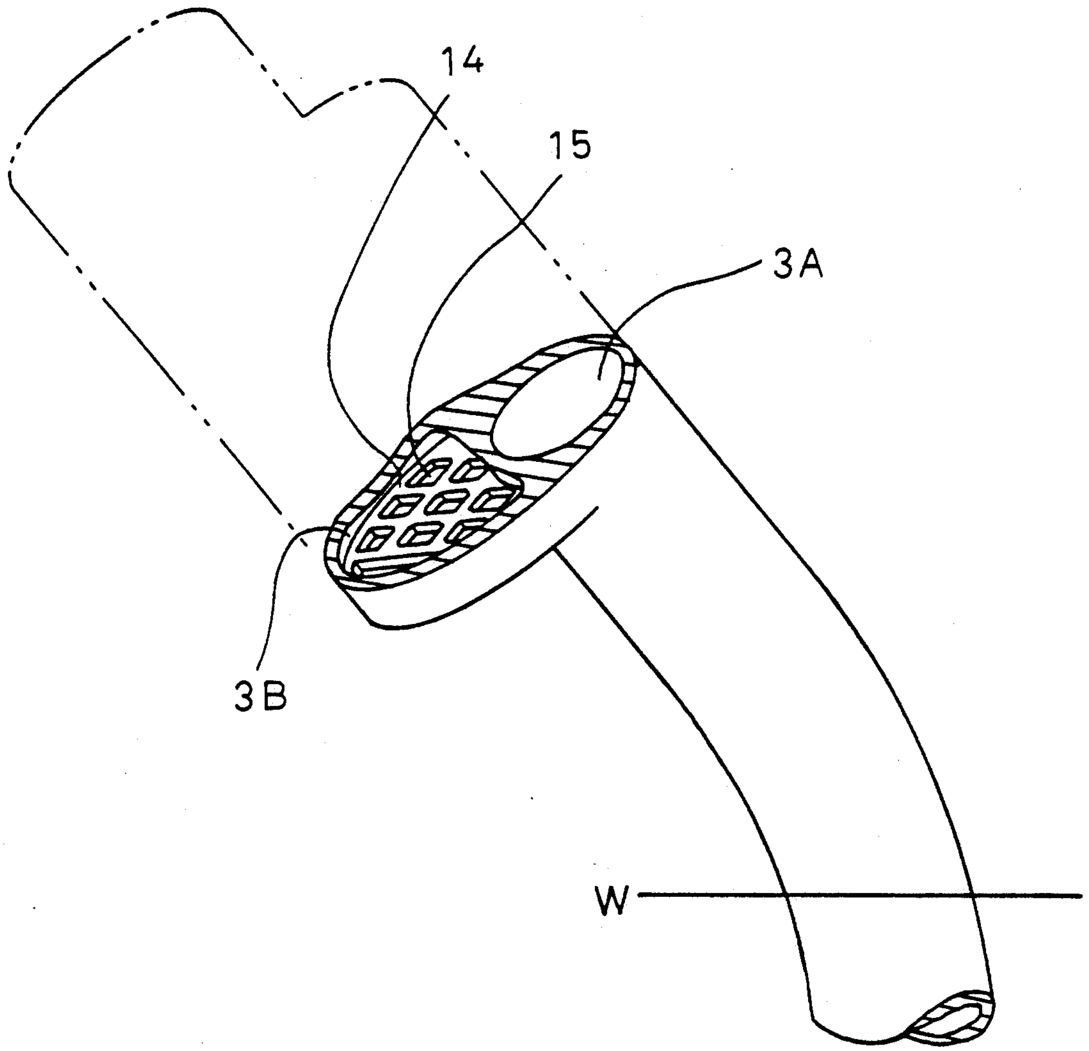
FIGS. 6 and 7 are partial cross sectional views of two other embodiments of the invention.

FIG. 6 illustrates another embodiment of the invention wherein the non-return valve 11 of FIGS. 2 and 3 and the vanes 12 of FIGS. 4 and 5 have been replaced with a grid structure 14 containing a plurality of openings 15. This grid structure 14 and openings 15 serve to partially obstruct the upward flow of water through said second pipe portion (3B).

Figure 7:
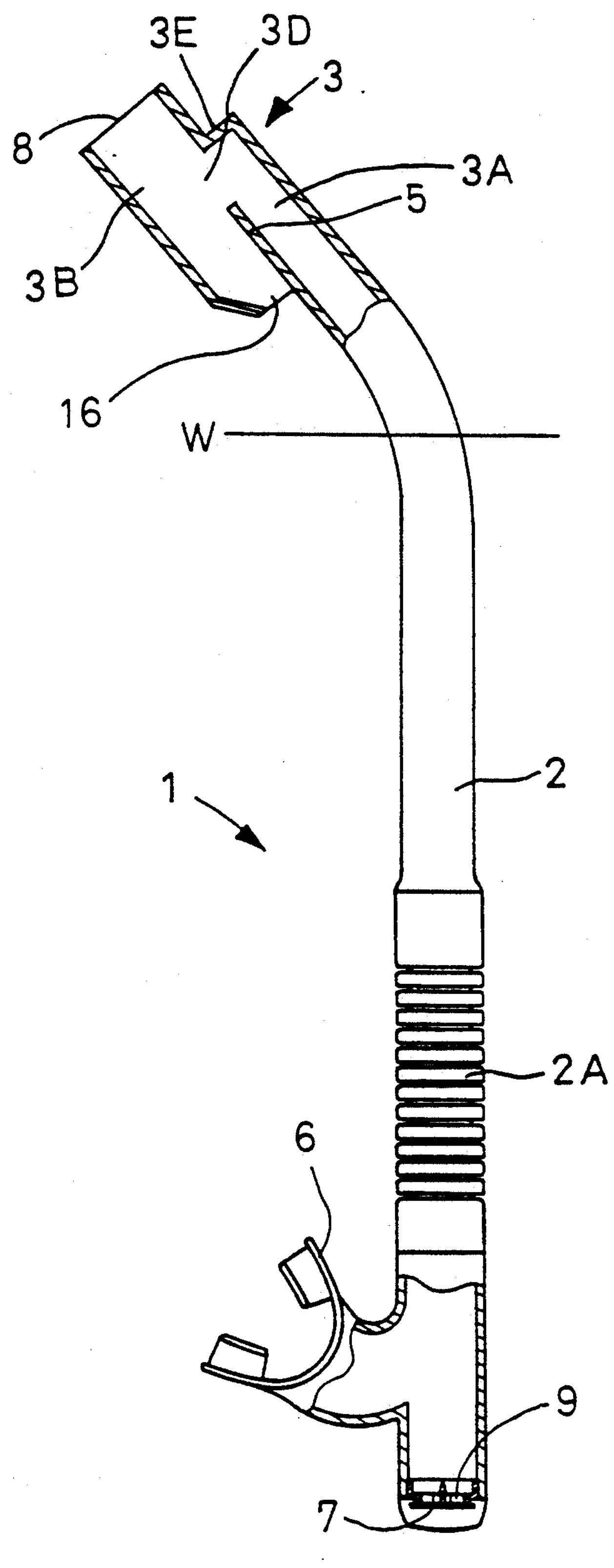

FIG. 7 illustrates another embodiment of the invention wherein the lower end 16 of the second pipe portion 3B is unobstructed.

What is claimed is:

1. A diving snorkel comprising a ventilating portion (3) provided with an air inlet (8) adapted to be positioned above the water surface, a mouthpiece (6) adapted to be positioned below the water surface, a draining portion (9) provided with a first non-return valve (7) and adapted also to be positioned below the water surface during use of the snorkel, said first non-return valve (7) being adapted to be normally opened downward with respect to the water surface, and a main pipe (2) connecting said air inlet (8) to said mouthpiece (6) and said draining portion (9), wherein said ventilating portion (3) comprises a first pipe portion (3A) and a second pipe portion (3B) extending in parallel to each other and a communicating port (3D) laterally establishing a communication between said first and second pipe portions (3A and 3B) wherein said first pipe portion (3A) has an upper end provided with a top wall (3E) and a lower end connected integrally with said main pipe (2), wherein said second pipe portion (3B) has an upper end that is provided with said air inlet (8) and a lower end provided with a second non-return valve (11) adapted to be normally opened outward of said second pipe portion (3B) and wherein said communicating port (3D) is provided in said second pipe portion (3B) between said air inlet (8) and said second non-return valve (11).

2. A snorkel as recited in claim 1 wherein said first pipe portion (3A) and said second pipe portion (3B) have a common inner pipe wall (5) separating them from each other and said communicating port (3D) is defined at least partially by said common inner pipe wall (5).

3. A snorkel as recited in claim 2 wherein said top wall (3E) of said first pipe portion (3A) extends obliquely with respect to the central axis of said first pipe portion (3A) so that said air inlet (8) is defined at least partially by said top wall (3E) as well as the upper end of said second pipe portion (3B).

4. A diving snorkel comprising a ventilating portion (3) provided with an air inlet (8) adapted to be positioned above the water surface, a mouthpiece (6) adapted to be positioned below the water surface, a draining portion (9) provided with a first non-return valve (7) that is also adapted to be positioned below the water surface during use of the snorkel, said first non-return valve (7) being adapted to be normally opened downward with respect to the water surface, and a main pipe (2) connecting said air inlet (8) to said mouthpiece (6) and said draining portion (9) wherein said ventilating portion (3) comprises (a) a first pipe portion (3A) having an upper end, a lower end and intermediate side walls, (b) said first pipe portion (3A) having a top wall (3E) at its upper end and having its lower end connected integrally with said main pipe (2), (c) a second pipe portion (3B) having an upper end, a lower end and intermediate side walls, said second pipe portion (3B) being joined to said first pipe portion (3A) in a side-by-side arrangement so that said pipe portions (3A and 3B) have a common side wall section, (d) the upper end of said second pipe portion (3B) being provided with said air inlet (8), (e) the lower end of said second pipe portion (3B) being provided with an outlet that can carry away at least a portion of any downward drainage of water entering the upper end of said second pipe portion (3B) so that such water will not enter said first pipe portion (3A), and (f) a communicating port (3D) which establishes communication between said first and second pipe portions (3A and 3B), said port (3D) being located intermediate said air inlet (8) and the outlet set forth in (e), said second pipe portion (3B) serving as an obstruction which will inhibit the washing of water into said communicating port (3D) as the snorkel is moved through the water.

5. A diving snorkel according to claim 4 wherein the lower end of said second pipe portion (3B) contains a second non-return valve (11) which is adapted to be normally opened outward of said second pipe portion (3B).

6. A diving snorkel according to claim 4 wherein said outlet in (e) contains a plurality of spaced apart vanes (12) which partially obstruct the upward flow of water through said second pipe portion (3B).

7. A diving snorkel according to claim 4 wherein said outlet in (e) is provided with a grid structure containing a plurality of openings, said grid structure serving to partially obstruct the upward flow of water through said second pipe portion (3B).

* * * * *